(12) United States Patent
Gertsenchtein

(10) Patent No.: US 11,179,518 B2
(45) Date of Patent: Nov. 23, 2021

(54) SYRINGE SHIELD ASSEMBLY FOR HOUSING AND TRANSPORTING A SYRINGE CONTAINING RADIOACTIVE DRUG

(71) Applicant: JUBILANT DRAXIMAGE INC., Kirkland (CA)

(72) Inventor: Michael Gertsenchtein, Kanata (CA)

(73) Assignee: JUBILANT DRAXIMAGE INC.

( * ) Notice: Subject to any disclaimer, the term of this patent is extended or adjusted under 35 U.S.C. 154(b) by 146 days.

(21) Appl. No.: 16/803,098

(22) Filed: Feb. 27, 2020

(65) Prior Publication Data

US 2021/0268187 A1 Sep. 2, 2021

(51) Int. Cl.
| | | |
|---|---|---|
| *A61M 5/31* | (2006.01) | |
| *A61M 5/32* | (2006.01) | |
| *G21F 5/00* | (2006.01) | |
| *A61M 5/178* | (2006.01) | |
| *G21F 5/018* | (2006.01) | |

(52) U.S. Cl.
CPC ........ *A61M 5/1785* (2013.01); *A61M 5/3129* (2013.01); *A61M 5/3204* (2013.01); *G21F 5/018* (2013.01); *A61M 2005/3131* (2013.01)

(58) Field of Classification Search
CPC .............. A61M 5/1785; A61M 5/3129; A61M 5/3204; A61M 2005/3131; G21F 5/018
USPC ......... 250/505.1, 506.1, 507.1, 515.1, 516.1, 250/517.1, 518.1, 519.1
See application file for complete search history.

(56) References Cited

U.S. PATENT DOCUMENTS

| | | | | |
|---|---|---|---|---|
| 2009/0072169 | A1* | 3/2009 | Polsinelli ............ | A61M 5/1785 250/515.1 |
| 2009/0270672 | A1* | 10/2009 | Fago ...................... | G21F 5/018 600/5 |
| 2019/0080808 | A1* | 3/2019 | Schreuder ............... | A61J 3/075 |
| 2021/0213301 | A1* | 7/2021 | Akerele-Ale ..... | A61M 25/0108 |

* cited by examiner

*Primary Examiner* — Nicole M Ippolito
(74) *Attorney, Agent, or Firm* — Lavery, De Billy, LLP; Gonzalo Lavin

(57) ABSTRACT

Syringe shield (2) includes a barrel housing (4), which includes: a barrel housing (6) with a radiation-shielding material, a first open end (8), and a second open end (10); and a removable cover (12) which is slidably connectable to the barrel housing (6). The removable cover (12) includes an end cap (14) which covers the second open end (10) when the removable cover (12) is slidably connected to the barrel housing (6). The barrel housing (4) also includes a plunger housing (16) with a radiation-shielding material. A first end (18) of the plunger housing (16) is open and is connectable to the first open end (8) of the barrel housing (4), and a second end (20) of the plunger housing (16) includes a top cap (22).

23 Claims, 15 Drawing Sheets

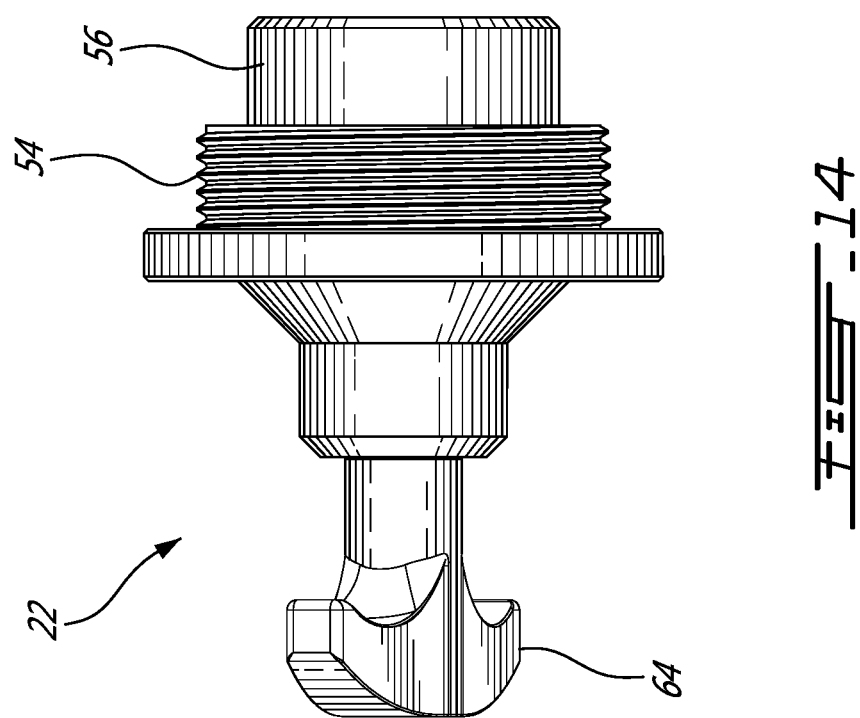

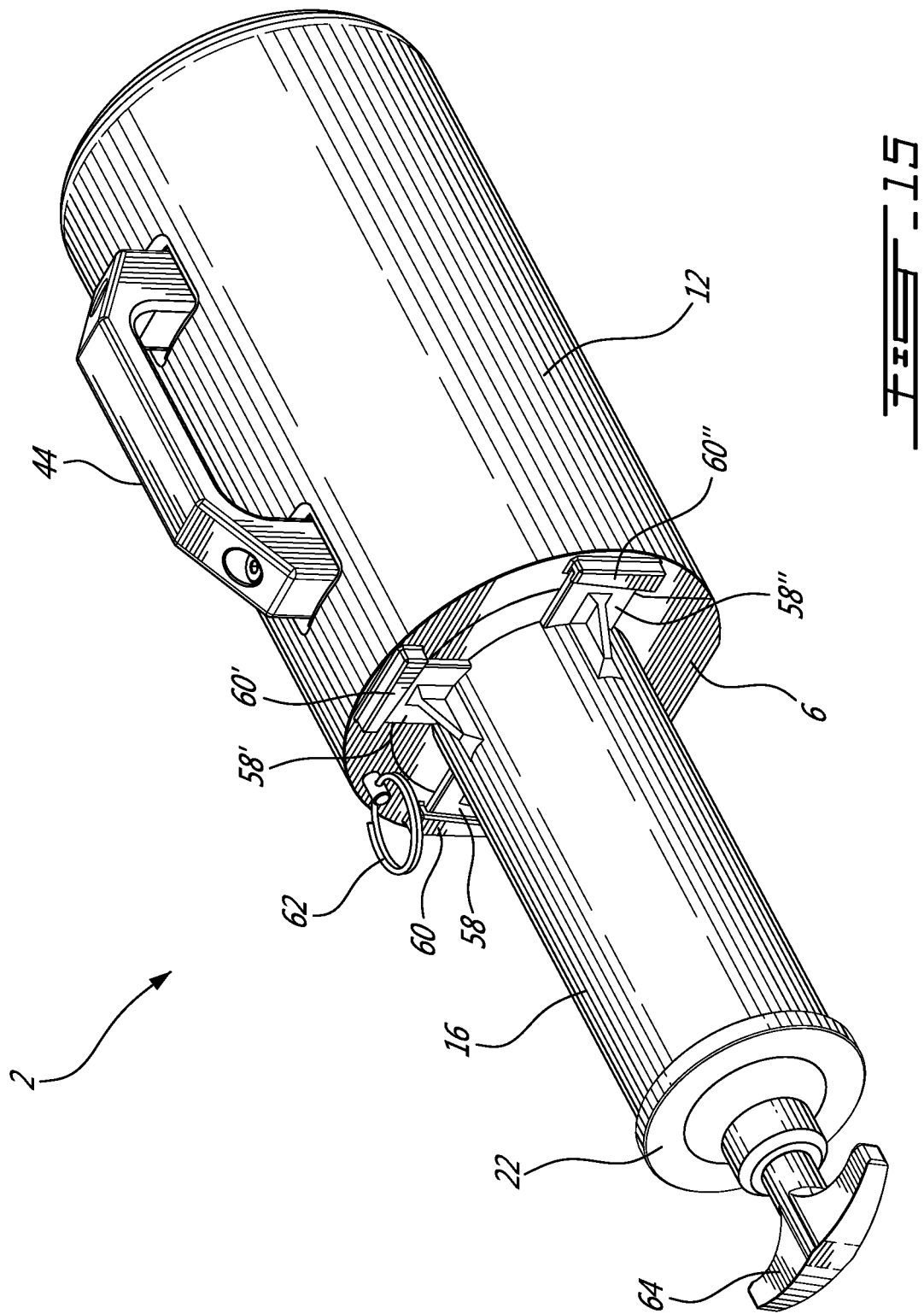

SYRINGE SHIELD ASSEMBLY FOR HOUSING AND TRANSPORTING A SYRINGE CONTAINING RADIOACTIVE DRUG

FIELD OF THE INVENTION

The present invention relates to intravenous radioactive drug delivery and transportation, and more particularly to a syringe shield for housing and transporting a syringe containing radioactive drug.

BACKGROUND OF THE INVENTION

Radioactive drugs, such as metaiodobenzylguanidine (MIBG) combined with radioactive iodine (1-131), are often used in the treatments of cancers and other such afflictions. Typically, these drugs are produced in a specialty pharmacy, packaged in syringes, then transported to medical facilities so that they can be administered to a patient in need. While effective, these drugs pose numerous dangers to various health care and nuclear medicine personnel responsible for its fabrication, transportation, handling and usage. In particular, the medical professionals responsible for the administration of these drugs are at risk of exposure to radioactivity, which may be hazardous for their health. As such, it is essential that the syringes containing these radioactive drugs are covered by a shield-type enclosure fabricated from a material that prevents excessive radioactivity from escaping the syringe to the surrounding environment.

While various syringe shields currently exist, they are typically designed for lower activity—mostly diagnostic doses and sized to house syringes whose volumetric capacities are insufficient to contain a full dose of the high energy radioactive drug. As such, multiple syringes are needed, which requires additional shields and added manipulation steps which complicate and add time to the treatment procedures with additional radiation exposure to workers and contamination.

In addition, current syringe shields typically cover the barrel of the syringe and leave the plunger and the tip of the syringe accessible for manipulation. As a result, radiation will emit therefrom. Moreover, the current syringe shields are generally round shapes, which can be dangerous due to the risk of them rolling off of a flat surface such as a table, creating a crushing hazard and a spill hazard.

SUMMARY OF THE INVENTION

According to the present invention, there is provided a syringe shield for housing a syringe containing a radioactive drug, the syringe comprising a barrel housing comprising a radiation-shielding material, a first open end, and a second open end, wherein the tip of the syringe is adjacent to or extends out from the second open end when the syringe is housed in the syringe shield; a removable cover that is removably connectable to the barrel housing so as to cover the second open end, as well as the tip of the syringe when the syringe is housed in the syringe shield, and so as to at least partially surround the barrel housing, and a plunger housing comprising a radiation shielding material and having a first end that is open and is removably connectable to the removable cover so as to enclose the barrel housing therebetween and, when the syringe is housed in the syringe shield, allow the plunger of the syringe to extend through the first open end of the barrel housing and into the plunger housing via the first end of the plunger housing.

BRIEF DESCRIPTION OF THE DRAWINGS

FIG. 14 shows a side view of the top cap of the plunger housing of the syringe shield of FIG. 1.
FIG. 15 shows a perspective view of an assembled syringe shield according to another embodiment of the present invention.

DETAILED DESCRIPTION

Figure 1:
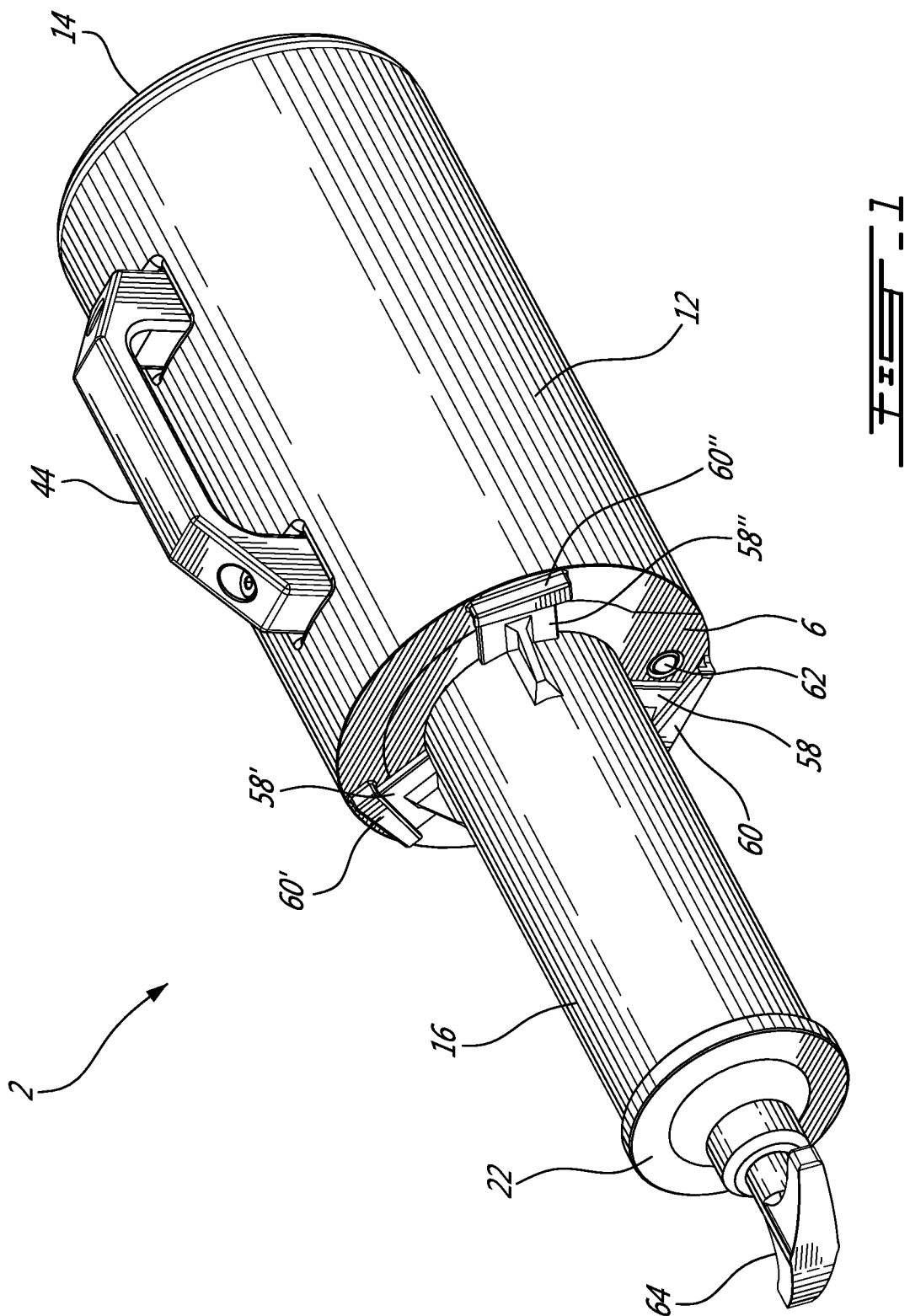
FIG. 1 shows a perspective view of an assembled syringe shield according to an embodiment of the present invention.

Based on the aforementioned drawbacks, it is an object of the present invention to provide a radioactive drug device that limits exposure to radioactivity during transportation and drug delivery while minimizing the required manual manipulation steps.

It is yet another object of the present invention to provide a syringe shield large enough to house a syringe containing a complete dosage of a radioactive drug for a given treatment.

It is yet another object of the present invention to provide a syringe shield with sufficient shielding to permit high energy (up to 1 Ci dose) shielding, enabling transportation as a YII (Yellow II) Label for Transportation of Radioactive Material. The YII Label implies the product for transportation meets the following criteria: i) a surface radiation level that does not exceed 50 millirems/hour, and ii) a radiation level at 1 meter that does not exceed 1 millirem/hour. The final packaging that includes the syringe shield and the package for shipment is preferably dimensioned to ease of the transporter. The package for shipment preferably comprises a cartridge box containing a rigid foam having a recess that is shaped to receive the shipment item, i.e. the syringe shield, so that movement of the shipped item within the box is prevented. Any other package for shipment is included within the scope of the invention.

It is yet another object of the present invention to provide a syringe shield shaped to prevent the syringe shield from rolling when placed on a flat surface.

In order to address the above and other drawbacks, a syringe shield is provided.

The present invention is illustrated in further details by the following non-limiting examples.

Referring to FIGS. 1-4, there is shown an embodiment of the syringe shield 2 of the present invention. The syringe shield 2 includes:

- a barrel housing 6 comprising a radiation-shielding material, a first open end 8, and a second open end 10;
- a removable cover 12, the removable cover 12 being removably connectable to the barrel housing 6 such that the removable cover 12 covers the second open end 10 and such that
- the removable cover 12 at least partially surrounds the barrel housing 6, and
- a plunger housing 16 comprising a radiation-shielding material, and having a first end 18 that is open and is removably connectable to the removable cover 12 so as to enclose the barrel housing 6 therebetween.

In the embodiment of the invention shown in FIGS. 1-14, the removable cover 12 partially surrounds the barrel housing 6 so as to leave the underside 36 of the barrel housing 6 uncovered. However, in embodiments the underside 36 of the barrel housing 6 may be covered by the removable cover 12.

Figure 5:
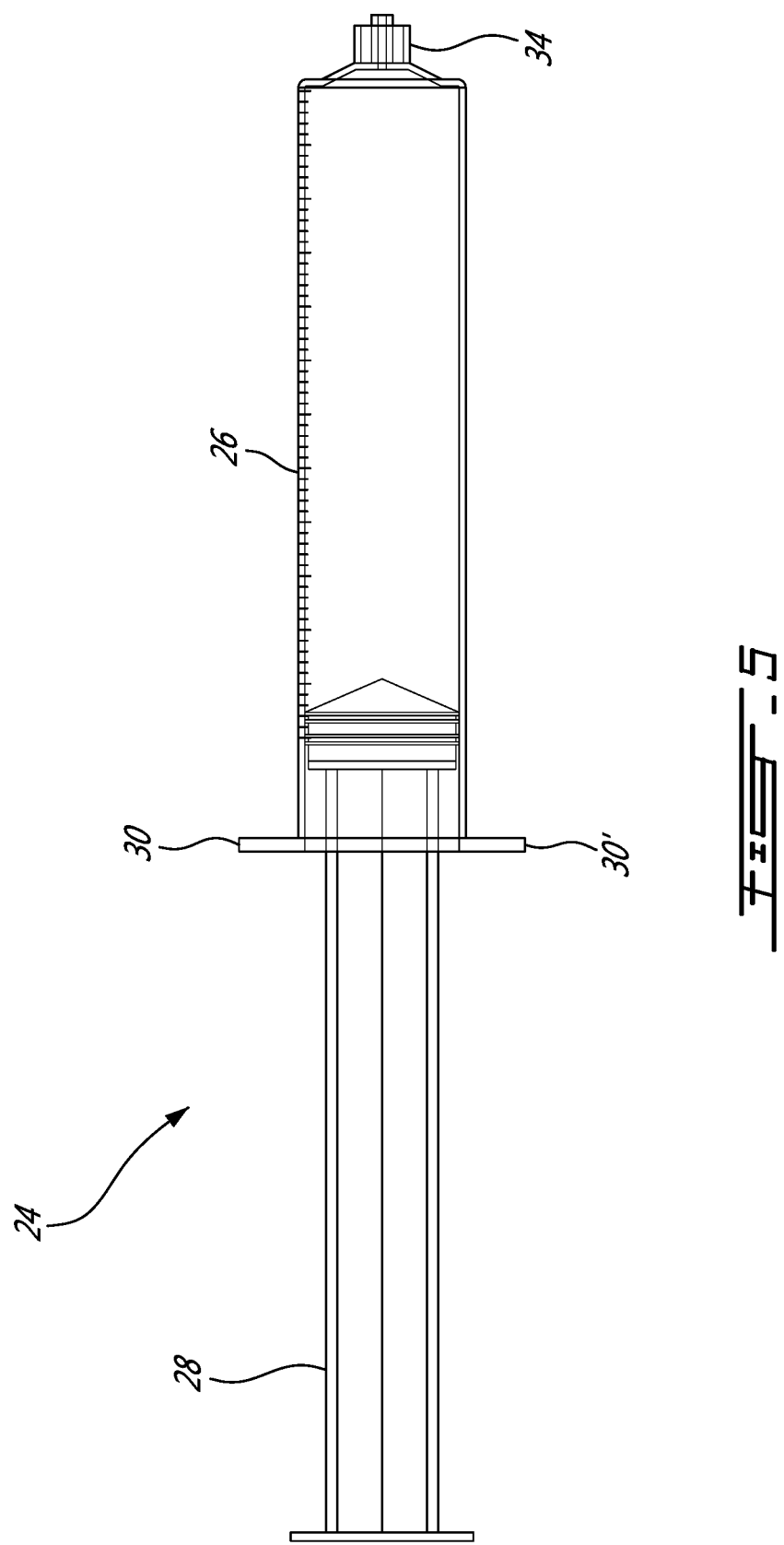
FIG. 5 shows a side view of a syringe which can be used with the syringe shield of the present invention.

The syringe shield 2 is typically used for housing a syringe 24 containing a radioactive drug, such as the syringe 24 shown in FIG. 5. Referring to FIG. 5, there is shown a syringe 24 including a barrel 26 containing the radioactive drug, a plunger 28 with at least one plunger flange 30, 30', and a tip 34. The syringe shield 2 is configured such that, when the syringe 24 is housed in the assembled syringe shield 2 (i.e. when the syringe 24 has been inserted into the assembled syringe shield 2), the tip 34 of the syringe 24 is adjacent to or extends out from the second open end 10 of the barrel housing 6, the removable cover 12 covers the tip 34 of the syringe 24, and the plunger 28 of the syringe 24 is extendable through the first open end 8 of the barrel housing 6 and into the plunger housing 16 via the first end 18 of the plunger housing 16. Preferably, the tip 34 of the syringe 24 is accessible from the second open end 10 by being adjacent to or by extending out from the second open end 10 of the barrel housing 6.

In embodiments, the syringe shield 2 of the present invention can be easily disassembled and reassembled, depending on whether a user wishes to insert a syringe 24 into the syringe shield 2, or whether a user wishes to remove or refill the syringe 24 from the syringe shield 2.

To assemble or reassemble the syringe shield 2, in an embodiment of the present invention, the removable cover 12 can be connected to the barrel housing 6. If a syringe 24 is to be inserted into the syringe shield 2, it can be inserted into the barrel housing 6 before or after the removable cover 12 has been connected thereto. The plunger housing 16 can then be releasably attached to the removable cover 12 to form the syringe shield 2. When the removable cover 12 is connected to the barrel housing 6, and when the plunger housing 16 is connected to the removable cover 12, the radioactivity contained in the syringe 24 is completely shielded from any angle.

When a user wishes to disassemble the syringe shield 2, for example to refill, remove, or use the syringe 24, the plunger housing 16 can be disconnected from the removable cover 12, and the removable cover 12 can then be disconnected from the barrel housing 6, thereby leaving the barrel housing 6 with the syringe 24 partially contained therein. The syringe 24 in the barrel housing 6 can be advantageously used without being removed from the barrel housing 6. In this configuration, the plunger 28 can move freely from an extended position to a retracted position and vice-versa. In this configuration, the tip 34 can be connected to a needle or connected to a tubing line through a connector such as a luer lock connector, and the plunger 28 can be actuated by being pushed and pulled manually or through a pump.

Figure 6:
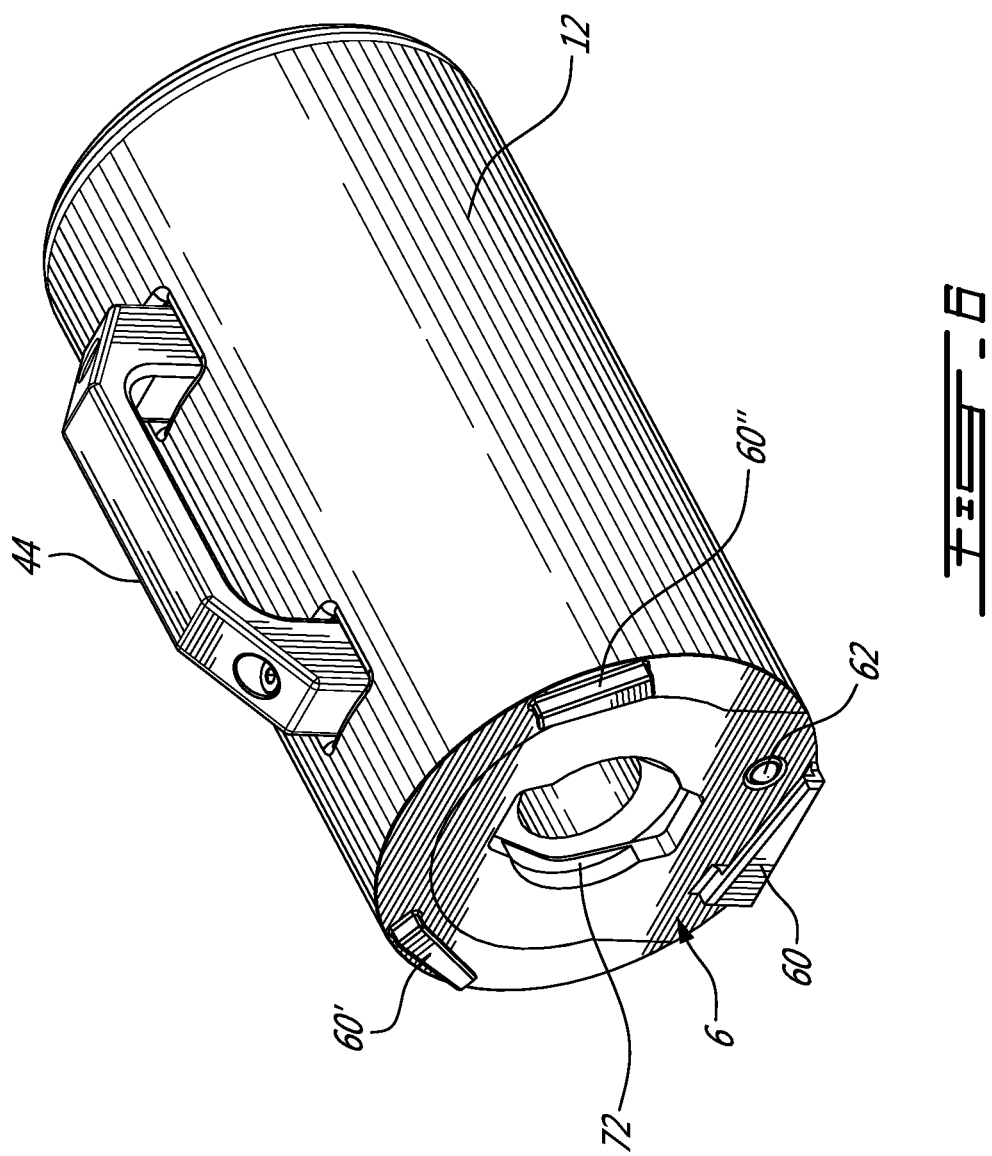
FIG. 6 shows a perspective view of the barrel housing and the removable cover of the syringe shield of FIG. 1.

Referring to FIG. 6, there is shown a barrel housing 6 and a removable cover 12 of an embodiment of the syringe shield 2 of the present invention. The removable cover 12 is removably connectable to the barrel housing 6, for example by being slidably connectable to the barrel housing 6, as shown for example in FIG. 6. However, the skilled person would understand that the removable cover 12 could be removably connected to the barrel housing 6 in a variety of ways, such as, for example: a threaded connection, a hinged connection, a pinned connection, through the use of magnetic catches, or mechanical latches. In embodiments, the removable cover 12 may be removably connected to the barrel housing 6 by means of a two-part shell that encloses the barrel housing 6 wherein the shell has a locking means to secure the closure of the two-part shell around the barrel housing, or by means of a shell that can partly enclose the barrel housing wherein the shell has locking means to secure the shell to the barrel housing, or any other embodiment that falls in the scope of the claims.

Figure 7:
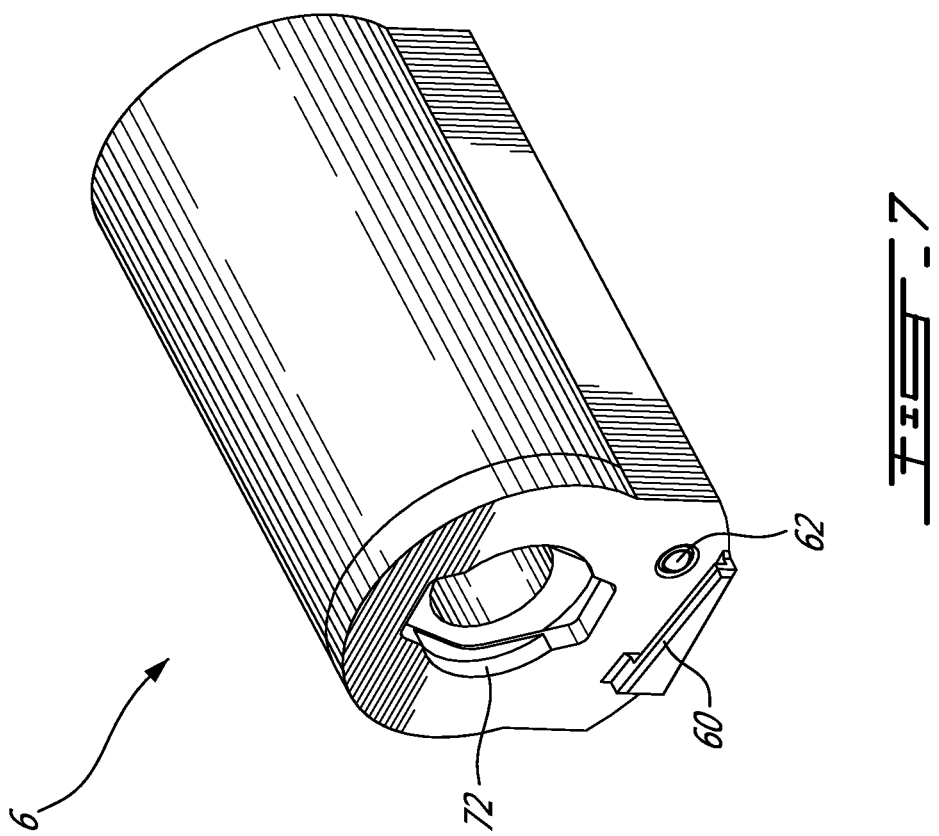
FIG. 7 shows a perspective view of the barrel housing of the syringe shield of FIG. 1.
Figure 8:
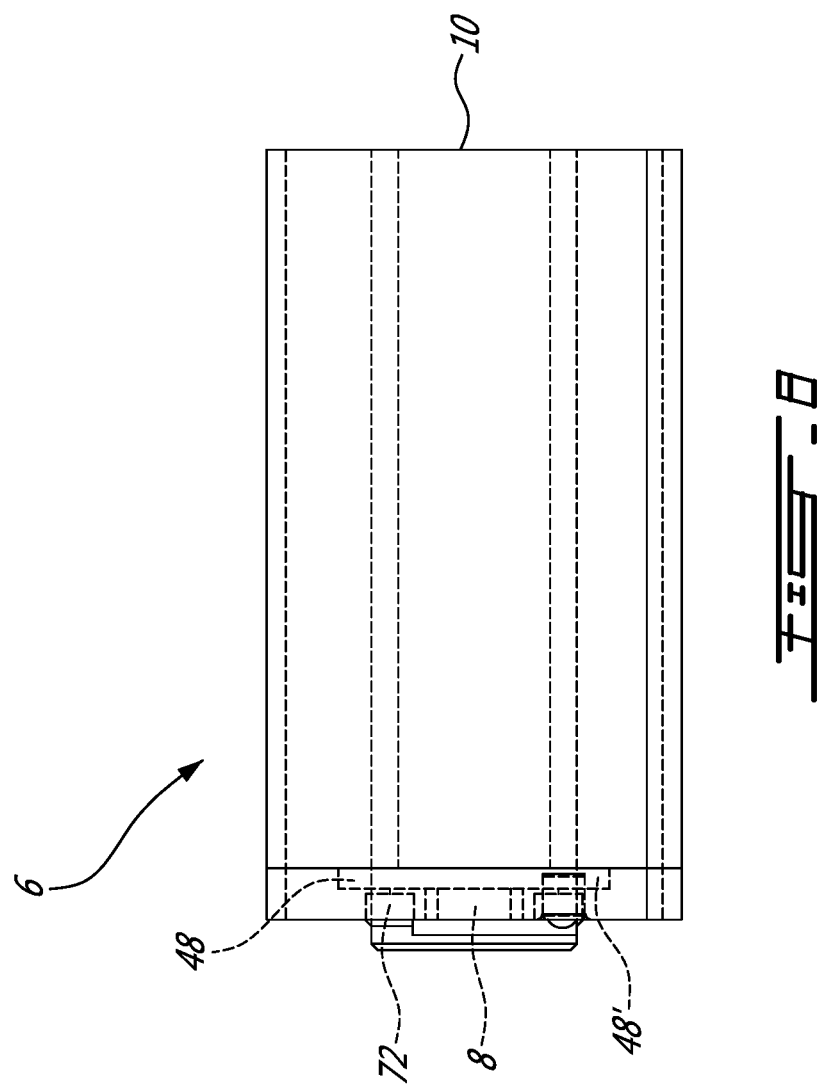
FIG. 8 shows a cross-sectional top view of the barrel housing of the syringe shield of FIG. 1.

Referring to FIGS. 7 and 8, there is shown a barrel housing 6 of an embodiment of the syringe shield 2 of the present invention. The barrel housing 6 of the syringe shield 2 is for housing the barrel 26 of the syringe 24 when the syringe 24 is placed inside the syringe shield 2. As stated, the barrel housing 6 comprises a radiation shielding material, a first open end 8, and a second open end 10. The syringe 24 is insertable in the barrel housing 6 such that the plunger 28 is extendable through the first open end 8 and the tip 34 is accessible from the second open end 10. According to embodiments of the invention, the tip 34 of the syringe 24 can be adjacent to or extend out the second open end 10. Advantageously, the syringe 24 can be in use and in connection with a tubing line and a pump system while remaining located inside the barrel housing 6. Preferably, the barrel housing 6 provides high radiation shielding and emits radiation primarily through its first and second open ends 8 and 10.

In embodiments, when the syringe 24 is inserted into the syringe shield 2, the barrel 26 of the syringe 24 will rest inside the barrel housing 6, while the plunger 28 of the syringe 24, when in an extended position, will extend through the first open end 8 of the barrel housing 6, and the tip 34 of the syringe 24 will be accessible from the second open end 10 of the barrel housing 6.

Figure 3:
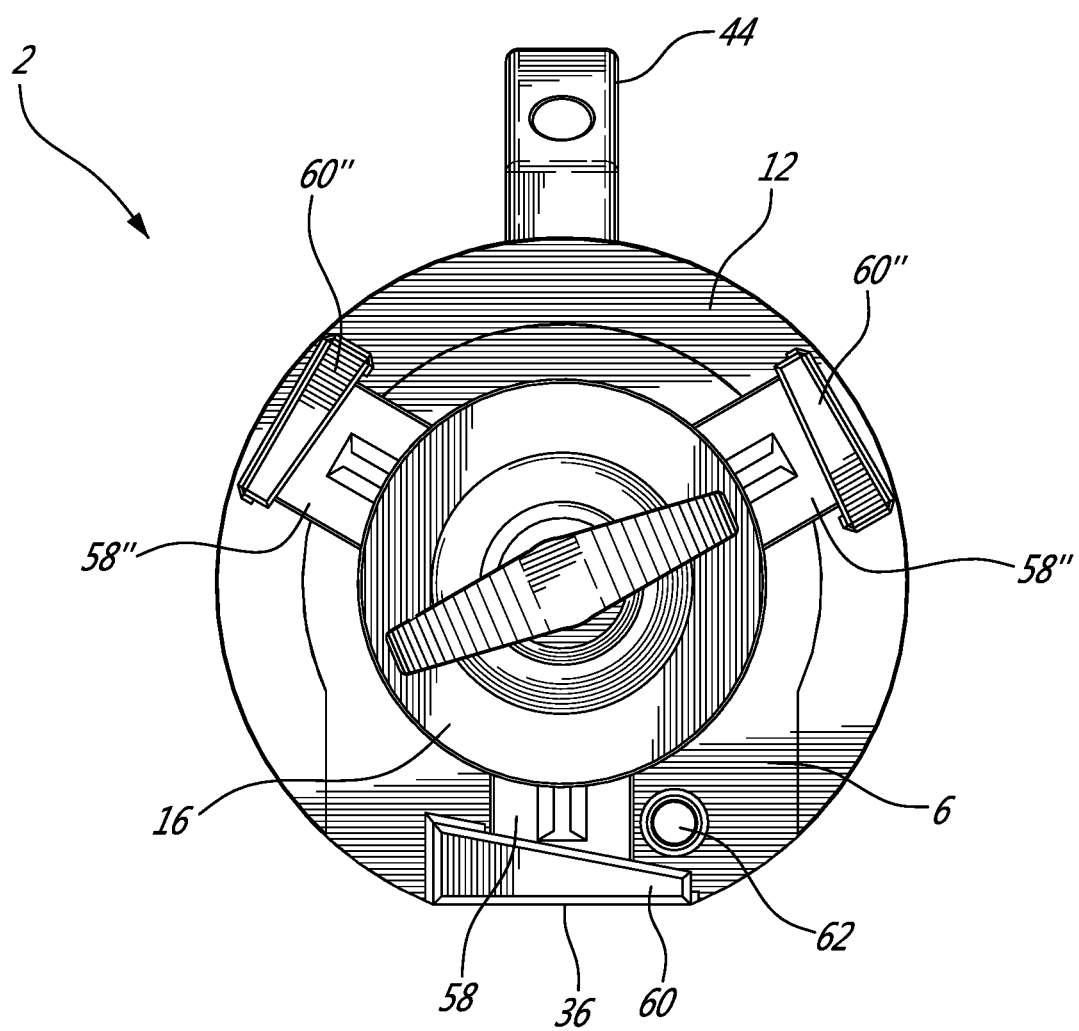
FIG. 3 shows a front view of the syringe shield of FIG. 1.
Figure 4:
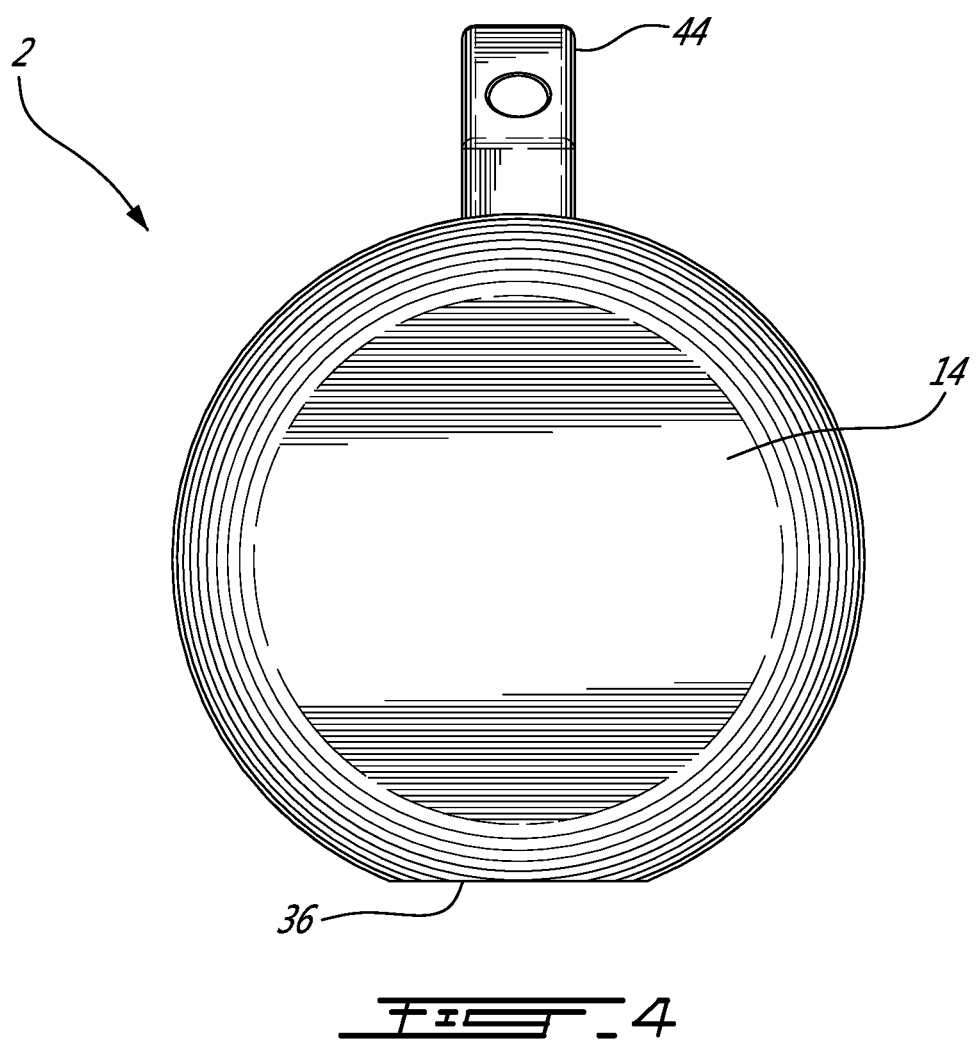
FIG. 4 shows a back view of the syringe shield of FIG. 1.

In an embodiment, and as shown for example in FIGS. 3 and 4, the underside 36 of the barrel housing 6 is shaped so as to prevent the barrel housing 6 from rolling, which thereby prevents the syringe shield 2 from rolling when placed on a flat surface. Preferably, the underside 36 of the barrel housing 6 is flat.

The syringe 24 is insertable through the first open end 8 of the barrel housing 6. The first open end 8 of the barrel housing 6 can also be shaped to receive at least one of the flanges 30, 30' of the plunger 28 of the syringe 24. The first open end 8 of the barrel housing 6 can also be designed to releasably engage with at least one of the flanges 30, 30' of the plunger 28. In a preferred embodiment, the first open end 8 of the barrel housing 6 is designed to releasably engage both flanges 30, 30'. For example, either of the flanges 30, 30' of the plunger 28 can function as a twist-lock element that, when twisted, will be received by a twist-lock flange receiver 48 or 48' in the barrel housing 6 (as shown for example in FIGS. 6 and 7), thereby better securing the syringe 24 to the barrel housing 6. To release the syringe 24, the syringe 24 need only be twisted in the opposite direction to disengage the plunger flanges 30, 30' from the twist-lock flange receivers 48 and 48'. According to a preferred embodiment, the flange receivers 48, 48' are one single element in the form of a round recess in the first open end 8.

Figure 9:
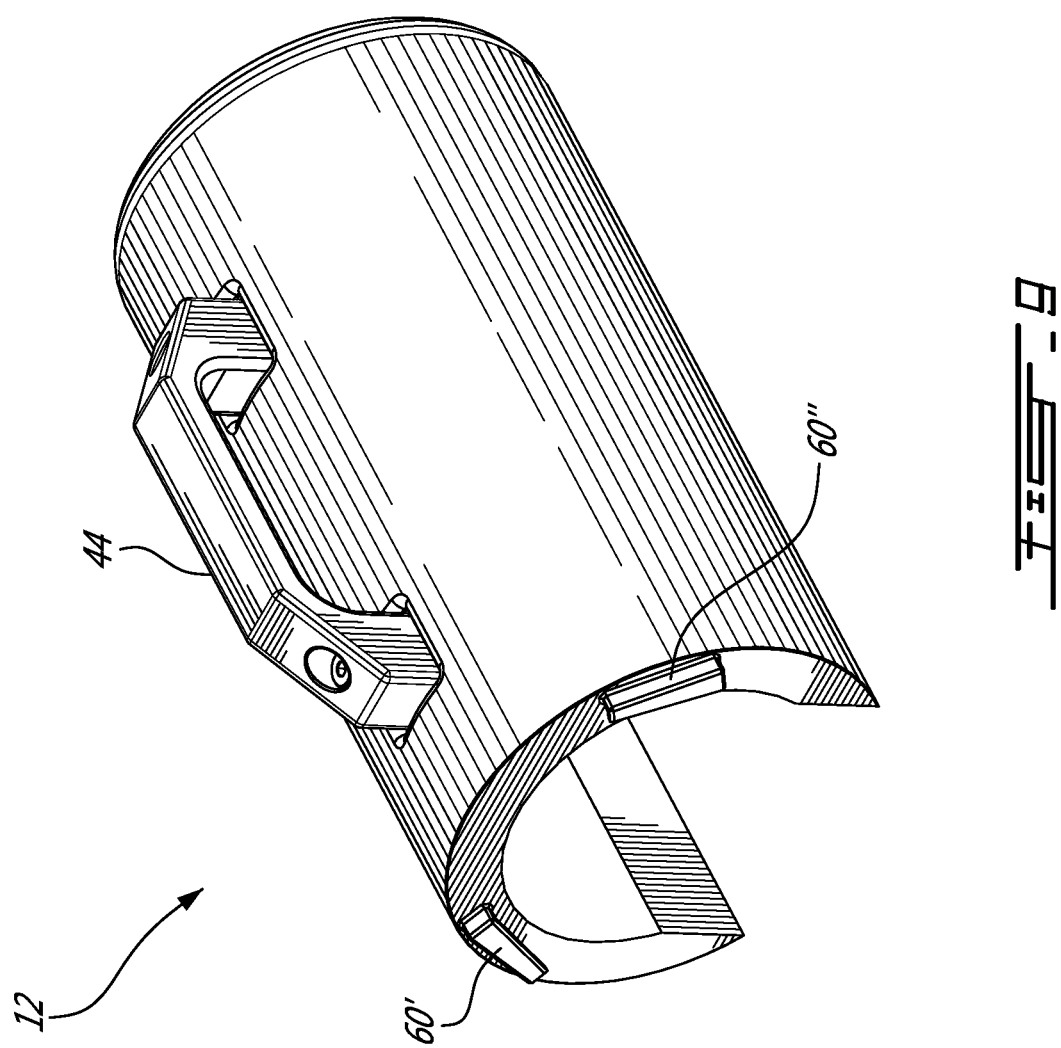
FIG. 9 shows a perspective view of the removable cover of the syringe shield of FIG. 1.
Figure 10:
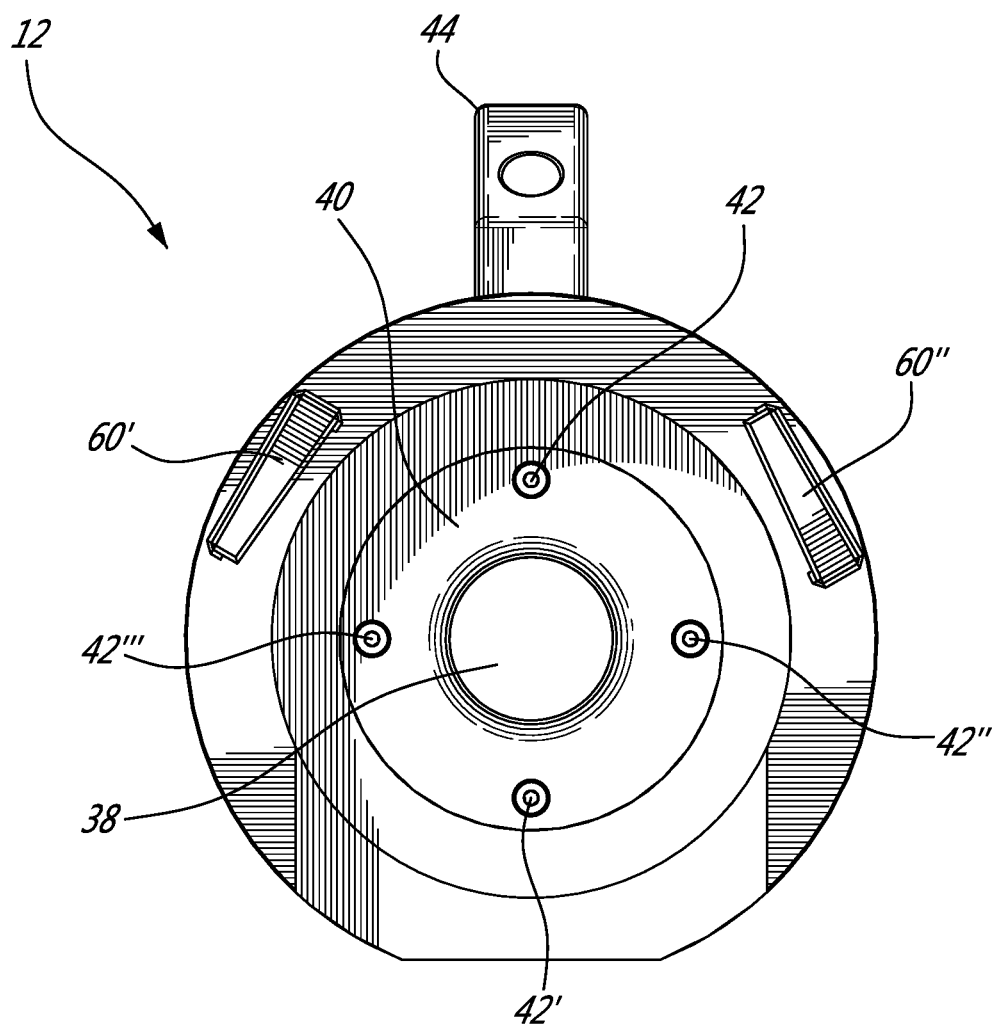
FIG. 10 shows a front view of the removable cover of the syringe shield of FIG. 1.

Referring to FIGS. 9 and 10, there is shown a removable cover 12 of an embodiment of the syringe shield 2 of the present invention. In embodiments, and as shown for example in FIG. 6, the removable cover 12 is shaped so as to cover all surfaces of the barrel housing 6 except the underside 36 of the barrel housing 6 and the first open end 8. This can allow the removable cover 12 to be removably connected to, preferably slidably mounted onto, the barrel housing 6 without having to lift the barrel housing 6, and without covering the first open end 8.

When the removable cover 12 is mounted on the barrel housing 6, the removable cover 12 will cover the second open end 10 of the barrel housing 6. In embodiments, when the removable cover 12 is removably connected to the barrel housing 6, the removable cover 12 will not be in direct contact with the second open end 10 of the barrel housing 6, thereby creating a gap 49 between the second open end 10 and the removable cover 12 (see for example FIG. 2). In embodiments, the removable cover 12 can shield radioactivity that is being emitted from the tip 34 of the syringe 24. Accordingly, the removable cover 12 can contain a radiation shielding material. In embodiments, the removable cover 12 comprises a puck 38 of radiation shielding material, preferably a tungsten puck, which covers the second open end 10 of the barrel housing 6 when the removable cover 12 is removably connected to the barrel housing 6. In embodiments, the puck 38 of radiation shielding material can be retained in the removable cover 12 by a covering plate 40, which can be secured to the removable cover 12 using screws 42, 42', 42'', 42''' for example, as shown for example in FIGS. 2 and 10.

Figure 2:
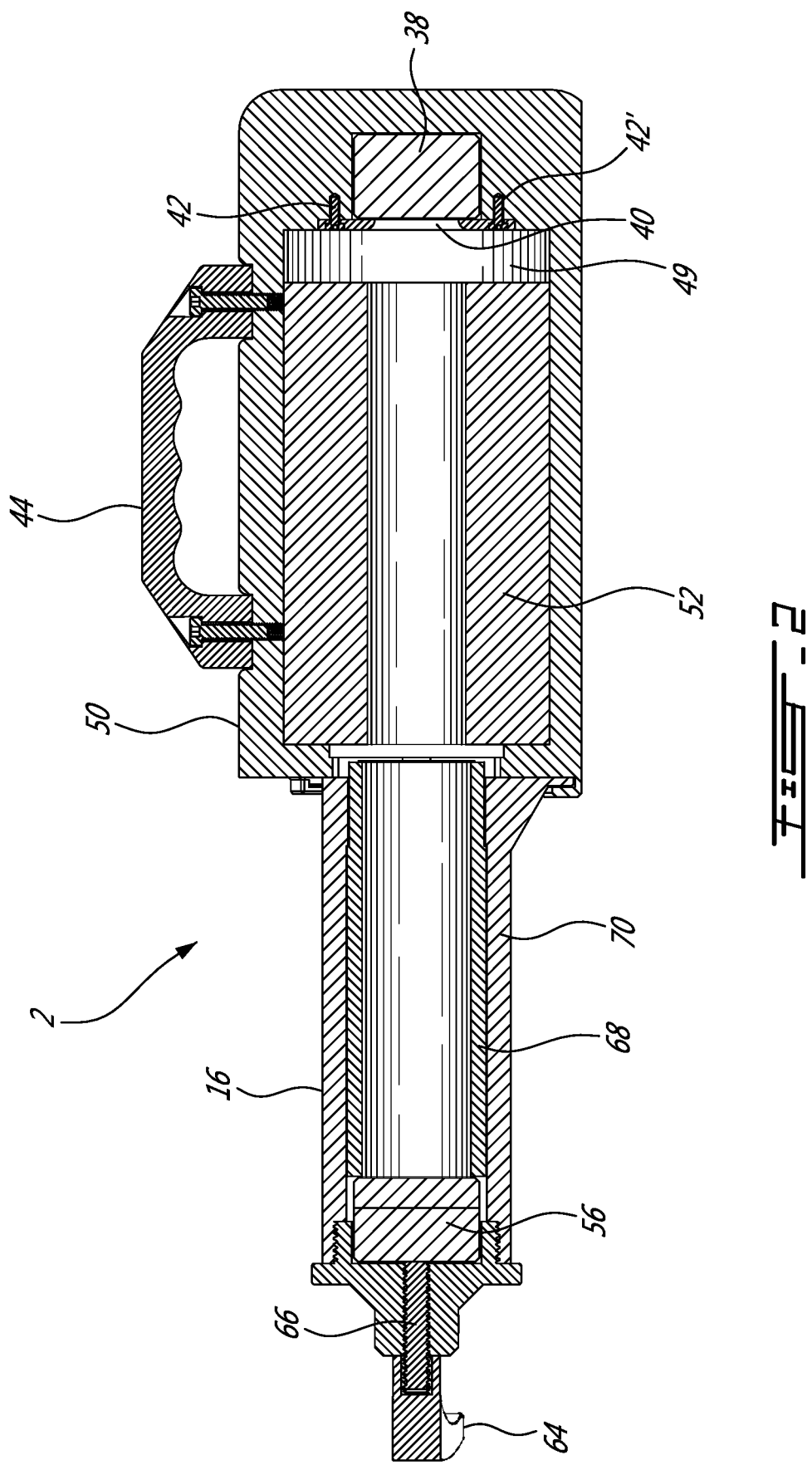
FIG. 2 shows a cross-sectional side view of the syringe shield of FIG. 1.

The removable cover 12 may further comprise a handle 44, preferably on the top side 50 thereof as shown in for example in FIG. 2. This handle 44 facilitates manipulating the removable cover 12, such as when it needs to be removed from or connected to the barrel housing 6. This handle 44 will also allow for a convenient way of carrying the syringe shield 2, once fully assembled. In addition, the handle 44, if placed on the top side 50 of the removable cover 12, will make it easier to orient the syringe shield 2, as the user would understand that the handle 44 indicates which side of the syringe shield 2 corresponds to the top side 50.

In embodiments, the removable cover 12 is shaped so that it can be slidably mounted onto the barrel housing 6 by sliding the removable cover 12 in a direction from the second open end 10 towards the first open end 8. As shown for example in FIG. 6, the removable cover 12 can be shaped to receive a partially cylindrically shaped barrel housing 6 with a flat underside 36. This can be achieved for example by having the removable cover 12 be shaped as a partially cylindrical shell, as shown for example in FIG. 9. In addition, with such a configuration, and due to the fact that the removable cover 12 covers the second end 10 of the barrel housing 6, the removable cover 12 can only be removed from the barrel housing 6 by sliding it in the opposite direction, meaning in a direction from the first open end 8 towards the second open end 10. However, it is to be understood that the removable cover 12 can be shaped and configured so as to be removably connectable to the barrel housing 6 in a number of manners. In an embodiment of the invention, the removable cover 12 can be disconnected from the barrel housing 6 without needing to manipulate or lift the barrel housing 6.

In an embodiment, the barrel housing 6 comprises radiation shielding material, preferably tungsten, and casing material, preferably stainless steel, while the removable cover 12 comprises casing material, preferably stainless steel, such that the barrel housing 6 and removable cover 12 can be connected together to form a casing, preferably a stainless steel casing, and a radiation shielding material internal layer 52, preferably a tungsten internal layer, as shown for example in FIG. 2. In another embodiment, the barrel housing 6 comprises radiation shielding material, preferably tungsten, and the removable cover 12 comprises casing material, preferably stainless steel.

Figure 11:
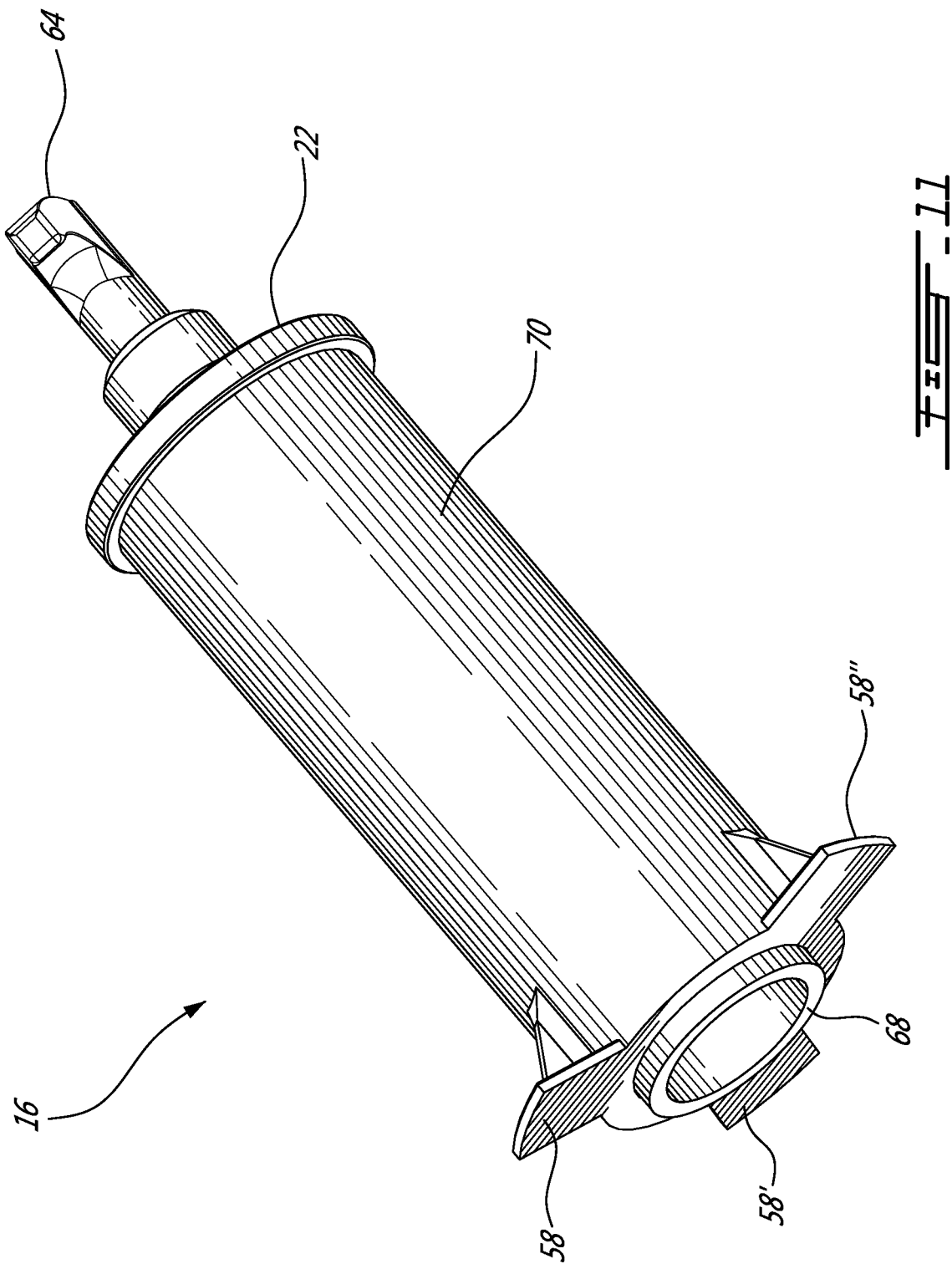
FIG. 11 shows a perspective view of the plunger housing of the syringe shield of FIG. 1.
Figure 12:
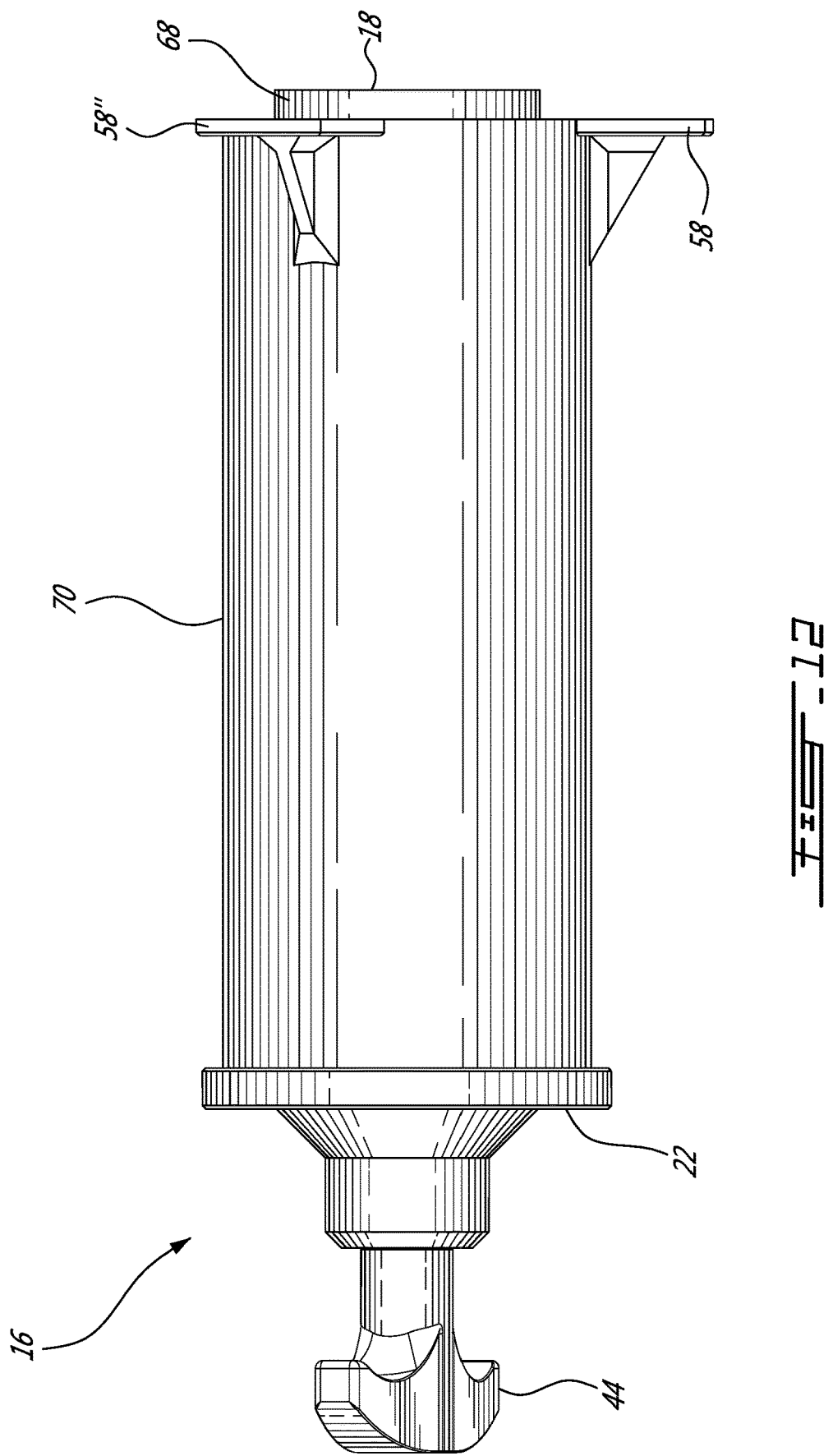
FIG. 12 shows a side view of the plunger housing of the syringe shield of FIG. 1.
Figure 13:
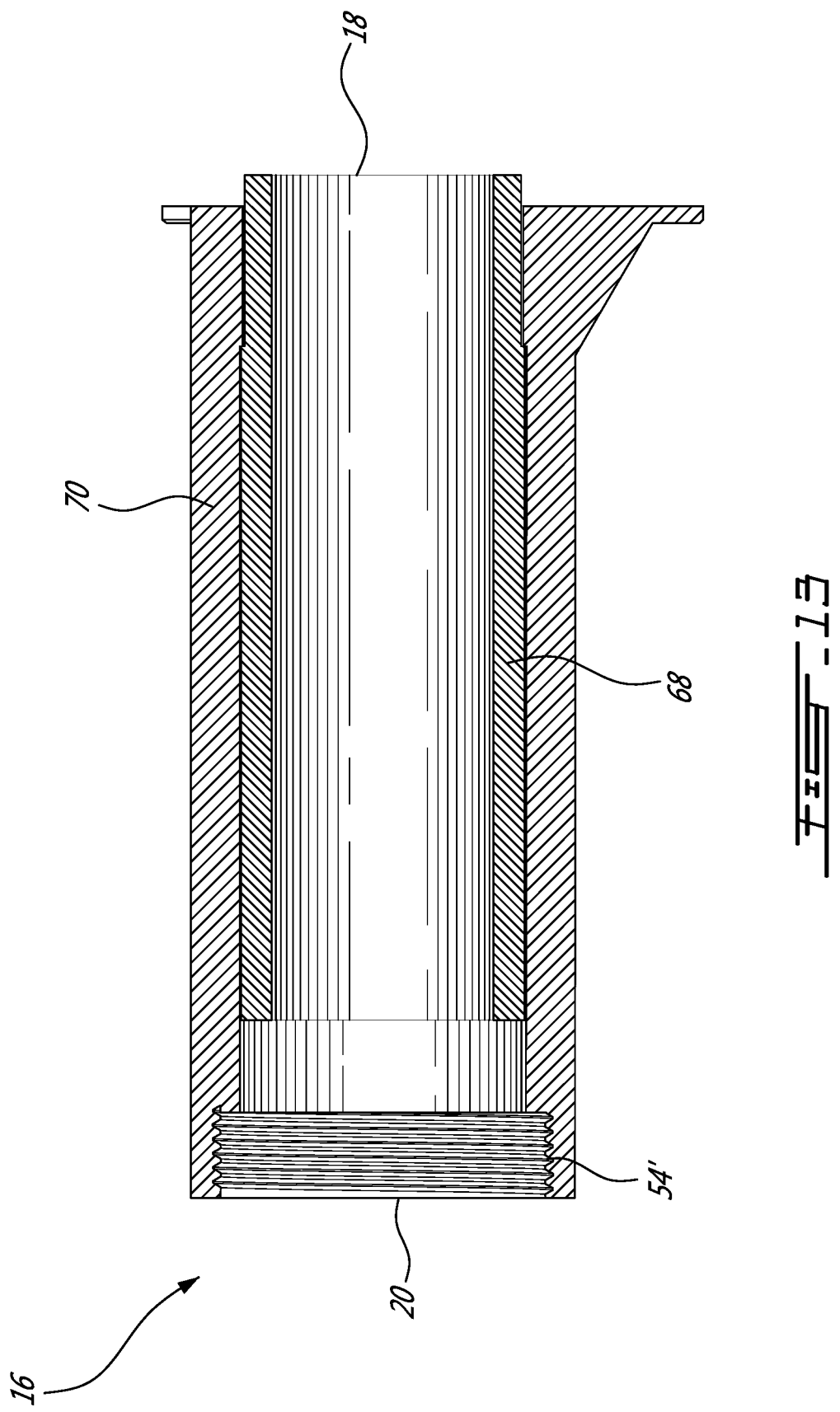
FIG. 13 shows a cross-sectional side view of the plunger housing of the syringe shield of FIG. 1, with the top cap having been removed.

Referring to FIGS. 11, 12, and 13, there is shown a plunger housing 16 of an embodiment of the syringe shield 2 of the present invention. The plunger housing 16 of the syringe shield 2 is for housing the plunger 28 of the syringe 24 when the plunger 28 is in an extended position. The plunger housing 16 comprises a first end 18 which is open and which is releasably connectable to the removable cover 12 so as to align with the first open end 8 of the barrel housing 6. As shown for example in FIG. 11, the plunger housing 16 may further comprise a top cap 22 releasably connected to a second end 20 thereof. In embodiments, and as can be seen for example in FIG. 2, the top cap 22 can be releasably secured to the plunger housing 16 via threaded connections. As such, the top cap 22 and the plunger housing 16 may each comprise a threaded section 54, 54'. It is to be understood that in embodiments comprising a removable top cap 22, if the top cap 22 were to be removed, the second end 20 of the plunger housing 16 would be open, as shown for example in FIG. 13.

Referring to FIG. 14, there is shown a top cap 22 of a plunger housing 16 of an embodiment of the syringe shield 2 of the present invention. In preferred embodiments, the top cap 22 is for shielding radioactivity from being emitted from the plunger 28 of the syringe 24. Accordingly, in such preferred embodiments, the top cap 22 will contain a radiation shielding material. In embodiments, the top cap 22 comprises a puck 56 of radiation shielding material, preferably a tungsten puck. In embodiments, and as shown for example in FIG. 2, the puck 56 of radiation shielding material can be retained in the plunger housing 16 by having a section of the plunger housing 16 possess a narrower diameter, thereby defining a cavity in the plunger housing 16 which will hold the puck 56 of radiation shielding material.

The plunger housing 16 can be releasably secured to the removable cover 12 and optionally the barrel housing 6 in a variety of ways, such as by using a twist-lock assembly, or any other mechanical connection such as, but not exclusively: a threaded connection, a hinged connection, a pinned connection, through the use of magnetic catches, or mechanical latches. In preferred embodiments, such as for example the embodiments shown in FIGS. 1 and 15, the plunger housing 16 is releasably secured to the removable cover 12 and optionally the barrel housing 6 by using a twist-lock assembly. For example, and as shown for example in FIG. 11, the plunger housing 16 may have a plurality of twist-lock elements 58, 58', 58'' extending radially from the first end 18 of the plunger housing 16. As shown for example in FIG. 3, these twist-lock elements 58, 58', 58'', when placed against the first open end 8 of the barrel housing 6 and twisted, can be received by twist-lock recesses 60, 60', 60'' in the removable cover 12 and optionally the barrel housing 6, thereby releasably connecting the plunger housing 16 to the removable cover 12 and optionally the barrel housing 6. In addition, securing the plunger housing 16 to the removable cover 12 and the barrel housing 6 will also better secure the barrel housing 6 to the removable cover 12; this occurs if for example both the removable cover 12 and the barrel housing 6 comprise twist-lock recesses 60, 60', 60" that receive twist-lock elements 58, 58', 58", as shown for example in FIG. 6. As also shown for example in FIG. 6, the barrel housing 6 and/or the removable cover 12 may further comprise a securing means 62 to better secure the plunger housing 16 by helping prevent the twist-lock elements 58, 58', 58" from unwantedly being twisted out of the twist lock recesses 60, 60', 60". In preferred embodiments, the securing means 62 are a spring plunger (FIG. 6), a locking pin (as shown for example in FIG. 15), or any of, but not limited to, magnetic catch, anchor, latch or dowel. In preferred embodiments, the securing means are a spring plunger or a locking pin.

Referring to FIG. 15, there is shown an embodiment of the syringe shield 2 of the present invention where the twist-lock elements 58, 58', 58" are received by twist-lock recesses 60, 60', 60" in the removable cover 12 alone, as opposed to being received by twist-lock recesses 60, 60', 60" in both the removable cover 12 and the barrel housing 6. In the embodiment shown in FIG. 15, the securing means 62 are a locking pin located on the barrel housing 6, as opposed to a spring plunger located on the removable cover 6 (as shown for example in FIG. 6).

In embodiments, as shown for example in FIG. 14, the top cap 22 comprises a handle 64, which allows for a convenient way of carrying the syringe shield 2 once fully assembled. In embodiments, the handle 64 can make it easier to remove the top cap 22 from the plunger housing 16. In embodiments, the handle 64 is secured to the top cap 22 with a screw 66, as shown for example in FIG. 2.

In an embodiment, and as shown for example in FIGS. 2 and 12, the plunger housing 16 comprises an inner layer 68, preferably a radiation shielding material inner layer, more preferably a tungsten inner layer, and an outer layer 70, preferably made of stainless steel. In a preferred embodiment, the removable cover 12 and the top cap 22 are each made of stainless steel and each comprise a puck of radiation shielding material, preferably a puck of tungsten.

In an embodiment, and as shown for example in FIGS. 2 and 12, the inner layer 68 can extend beyond the outer layer 70 at the first end 18. With such a configuration, and as shown for example in FIGS. 6 and 7, the barrel housing 6 may comprise a recess 72 whose diameter is sufficiently large to receive the inner layer 68 of the plunger housing 16, but not large enough to receive the outer layer 70. As shown for example in FIG. 2, the recess will receive the inner layer 68 when the plunger housing 16 is releasably attached to the removable cover 12 and optionally the barrel housing 6. This can help better secure the plunger housing 16 to the barrel housing 6. In addition, this can help the user guide the plunger housing 16 to the barrel housing 6, thereby making it easier to attach the plunger housing 16 to the removable cover 12 and optionally the barrel housing 6.

In an embodiment, the radiation-shielding material provides a proper shielding to the radioactive drug, wherein said radioactive drug has a radioactivity of up to 300 mCi, up to 350 mCi, up to 400 mCi, up to 450 mCi, up to 500 mCi, up to 550 mCi, up to 600 mCi, up to 700 mCi, up to 800 mCi, up to 900 mCi, or up to 1 Ci. Preferably, the radioactive drug having a radioactivity up to 1 Ci comprises iodine-131. The radiation shielding material may comprise tungsten, lead, stainless steel, aluminum alloy or a combination thereof.

In a preferred embodiment, the radiation-shielding material comprises tungsten. In an embodiment, the radiation-shielding material comprises a combination of lead and tungsten. In an embodiment, the radiation-shielding material comprises a combination of stainless steel and tungsten. In an embodiment, the radiation-shielding material comprises a combination of alloy and tungsten. In an embodiment, the radiation-shielding material comprises a combination of stainless steel, aluminum alloy and tungsten. The non-radiation shielding material may comprise stainless steel, aluminum alloy or a combination thereof.

In an embodiment, the syringe shield 2 is dimensioned to receive a syringe 24 containing up to one of thirty milliliters or sixty milliliters of the radioactive drug.

In an embodiment, the total weight of the syringe shield 2 is no more than 55 lbs, no more than 50 lbs, no more than 45 lbs, no more than 40 lbs, no more than 35 lbs, or no more than 30 lbs.

The present invention contemplates any combination of the embodiments and the preferred elements described therein. For conciseness, every combination is not recited therein although every combination is contemplated herein by the inventors and is thus encompassed the present disclosure. While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope, and spirit of this invention. The scope of the claims should not be limited by the preferred embodiments set forth in the examples, but should be given the broadest interpretation consistent with the description as a whole.

The invention claimed is:

1. A syringe shield for housing a syringe (24) containing a radioactive drug, the syringe (24) comprising a barrel (26) containing the radioactive drug, a plunger (28) and a tip (34), comprising:
   a barrel housing (6) comprising a radiation-shielding material, a first open end (8), and a second open end (10), wherein the tip (34) of the syringe (24) is adjacent to or extends out from the second open end (10) when the syringe (24) is housed in the syringe shield (2);
   a removable cover (12) that is removably connectable to the barrel housing (6) so as to cover the second open end (10), as well as the tip (34) of the syringe (24) when the syringe (24) is housed in the syringe shield (2), and so as to at least partially surround the barrel housing (6), and
   a plunger housing (16) comprising a radiation shielding material and having a first end (18) that is open and is removably connectable to the removable cover (12) so as to enclose the barrel housing (6) therebetween and, when the syringe (24) is housed in the syringe shield (2), allow the plunger (28) of the syringe (24) to extend through the first open end (8) of the barrel housing (6) and into the plunger housing (16) via the first end (18) of the plunger housing (16).

2. The syringe shield according to claim 1, wherein the plunger (28) of the syringe (24) comprises at least one plunger flange (30, 30'), and the first open end (8) of the barrel housing (6) is shaped to receive at least one plunger flange (30, 30').

3. The syringe shield according to claim 2, wherein the first open end (8) of the barrel housing (6) is configured to releasably engage with the at least one flange (30, 30') of the plunger (28).

4. The syringe shield according to claim 3, wherein at least one flange (30, 30') of the plunger (28) functions as a twist-lock element that, when twisted, is receivable by a twist-lock flange receiver (48, 48') in the barrel housing (6).

5. The syringe shield according to claim 1, wherein the removable cover (12) is configured to partially surround the barrel housing (6) so as to expose the underside (36) of the barrel housing (6) when the removable cover (12) is removably connected to the barrel housing (6), and wherein the underside (36) of the barrel housing (6) is shaped so as to prevent the barrel housing (6) from rolling when placed on a flat surface.

6. The syringe shield according to claim 5, wherein the underside (36) of the barrel housing (6) is flat.

7. The syringe shield according to claim 1, wherein the removable cover (12) is shaped so as to cover all surfaces of the barrel housing (6), except the underside (36) of the barrel housing (6) and the first open end (8), when the removable cover (12) is removably connected to the barrel housing (6).

8. The syringe shield according to claim 1, wherein the removable cover (12) comprises a puck (38) which comprises a radiation shielding material, wherein the puck (38) covers the second open end (10) of the barrel housing (6) when the removable cover (12) is removably connected to the barrel housing (6).

9. The syringe shield according to claim 1, wherein the removable cover (12) further comprises a handle (44).

10. The syringe shield according to claim 1, wherein the removable cover (12) is shaped so that it is slidably mountable onto the barrel housing (6) by sliding the removable cover (12) in a direction from the second open end (10) towards the first open end (8).

11. The syringe shield according to claim 1, wherein the removable cover (12) is shaped to receive a partially cylindrically shaped barrel housing (6) with a flat underside (36).

12. The syringe shield according to claim 1, wherein the removable cover (12) is shaped as a partially cylindrical shell.

13. The syringe shield according to claim 1, wherein the cover (12) is shaped so that said removable cover (12) can only be removed from the barrel housing (6) by sliding said removable cover (12) in a direction from the first open end (8) towards the second open end (10).

14. The syringe shield according to claim 1, wherein the barrel housing (6) comprises a cylindrical section made of radiation shielding material, and a base providing a flat underside (36).

15. The syringe shield according to claim 1, wherein the plunger housing (16) has an internal surface comprising a radiation shielding material.

16. The syringe shield according to claim 1, wherein the plunger housing (16) further comprises a top cap (22) that comprises a puck (56) of radiation shielding material.

17. The syringe shield according to claim 1, wherein the plunger housing (16) is releasably connectable to the removable cover (12) using a twist-lock assembly.

18. The syringe shield according to claim 1, wherein the plunger housing (16) is releasably connectable to the removable cover (12) and the barrel housing (6) using a twist-lock assembly.

19. The syringe shield according to claim 1, wherein the radiation shielding material comprises tungsten, lead, stainless steel, an aluminum alloy, or a combination thereof.

20. The syringe shield according to claim 1, wherein the radiation-shielding material comprises tungsten.

21. The syringe shield according to claim 1, wherein the syringe shield (2) is dimensioned to receive a syringe (24) containing up to thirty milliliters or up to sixty milliliters of said radioactive drug.

22. The syringe shield according to claim 1, wherein the total weight of the syringe shield (2) is no more than 55 lbs.

23. The syringe shield according to claim 1, wherein said radioactive drug has a radioactivity of up to 1 Ci, and the syringe shield has a radiation-shielding material that provides a shielding that meets the Yellow II label criteria for transportation of radioactive material.

* * * * *